United States Patent [19]
Zorayan et al.

[11] 4,307,079
[45] Dec. 22, 1981

[54] CONDENSATION PRODUCT OF GLYCIDOL ON FATTY CHAIN-CONTAINING DIGLYCOLAMIDES AND COSMETIC COMPOSITIONS CONTAINING THE SAME

[75] Inventors: Vahan Zorayan, Enghien-les-Bains; Raphael Gazrighian, Clichy-sous-Bois, both of France

[73] Assignee: L'Oreal, Paris, France

[21] Appl. No.: 735,216

[22] Filed: Oct. 22, 1976

[30] Foreign Application Priority Data

Oct. 23, 1975 [LU] Luxembourg .......................... 73633

[51] Int. Cl.³ .......................... A61K 7/06; A61K 7/48; C07C 103/38; C07C 103/60; C11D 1/722
[52] U.S. Cl. ..................................... 424/70; 252/548; 260/404; 424/47; 424/358; 424/365
[58] Field of Search .................... 260/404; 424/47, 70, 424/358, 365; 252/548

[56] References Cited

U.S. PATENT DOCUMENTS

| | | | |
|---|---|---|---|
| 2,002,613 | 5/1935 | Orthner et al. ................. | 260/404 X |
| 2,085,706 | 6/1937 | Schoeller et al. .................... | 260/404 |
| 2,089,569 | 8/1937 | Orthner et al. ...................... | 260/404 |
| 3,832,367 | 8/1974 | Heiba et al. ......................... | 260/404 |
| 3,875,197 | 4/1975 | Lorenz ............................... | 260/404 |
| 3,916,003 | 10/1975 | Suzuki et al. ....................... | 260/404 |

*Primary Examiner*—Natalie Trousof
*Assistant Examiner*—Vera C. Clarke
*Attorney, Agent, or Firm*—Cushman, Darby & Cushman

[57] ABSTRACT

Compounds of the formula

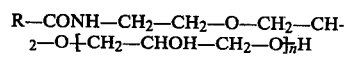

wherein R represents an aliphatic radical or mixture thereof, linear or branched, saturated or unsaturated, optionally carrying one or more hydroxyl groups, having from 8 to 30 carbon atoms, of natural or synthetic origin; and n representing a whole or decimal number from 1 to 5 represents the average degree of condensation.

15 Claims, No Drawings

CONDENSATION PRODUCT OF GLYCIDOL ON FATTY CHAIN-CONTAINING DIGLYCOLAMIDES AND COSMETIC COMPOSITIONS CONTAINING THE SAME

The present invention relates to non-ionic polyhydroxyl compounds obtained by the polycondensation of glycidol on fatty chain-containing diglycolamides, in the presence of an alkaline catalyst, to the process of preparing them and to their use as surface active agents, particularly in cosmetic compositions, for example, in foamy cosmetic compositions.

Non-ionic polyhydroxyl compounds obtained by the condensation of glycidol on fatty chain-containing α-diols, in the presence of an alkaline catalyst and their use in cosmetic compositions are disclosed in French Pat. No. 2,091,516 which essentially corresponds to U.S. Pat. Nos. 3,821,372; 3,928,224; 3,966,398 and U.S. application Ser. No. 678,030.

It has now been found, however, that the polyhydroxyl diglycolamides of the present invention provide a foam which is more unctuous than that provided by polyhydroxyl compounds prepared from alcohols or diols, and when employed in cosmetic compositions for the hair, the compounds of this invention render the hair softer than the said known compounds.

Further, the condensation of glycidol on certain organic compounds such as, amongst others, certain carboxylic amides, in the presence of an alkaline catalyst, is disclosed in U.S. Pat. No. 2,089,569. However, the process disclosed in this patent only provides products which are sufficiently water-soluble when a great excess of glycidol is employed.

Thus, in Example 4 of this patent wherein the initial organic compound reactant is a hydroxy ethylamide of copra fatty acids, 75 parts of glycidol, which corresponds to 10 moles of glycidol per mole of amide, are employed to solubilize 25 parts of this amide.

Thus, it is surprising to note that in accordance with the present invention a rapid addition of glycidol to fatty chain-containing diglycolamides at a temperature of about 100°-105° C., and advantageously at 130° C., and in the presence of an alkaline catalyst, and in particular alkaline hydroxides and alcoholates, and preferably sodium hydroxide, sodium methylate or potassium hydroxide, provides a reaction medium which remains perfectly homogeneous and also imparts water-solubility to the resulting product when as low as 1-5 moles of glycidol per mole of glycolamide are employed depending on the length of the fatty chain of said glycolamide.

The insufficient solubility of carboxylic amides prepared in accordance with the process of U.S. Pat. No. 2,089,569 can be explained by the fact that a great part of the glycidol, by self-condensing to form polyglycerols, is thus essentially not available for the condensation reaction. This self-condensation of glycidol is facilitated by the high temperature conditions recommended in said U.S. Pat. No. 2,089,569. Further prolonged heating favors degradation of the resulting products.

The present invention thus relates to compounds of the formula

wherein R represents an aliphatic radical or mixtures thereof, linear or branched, saturated or unsaturated, which optionally can be substituted by one or more hydroxyl groups, said radical having from 8 to 30 carbon atoms and being of synthetic or natural origin; and n represents a whole or decimal number from 1 to 5, which number designates the average degree of condensation.

Examples of radicals represented by R include octyl, nonyl, decyl, undecyl, dodecyl, tridecyl, tetradecyl, pentadecyl, hexadecyl, heptadecyl, octadecyl, eicosyl, and their mixtures; oleic or octadecenyl; a mixture of aliphatic radicals derived from the fatty acids of copra, topped fatty acids of copra, fatty acids of African oil palm, fatty acids of castor-oil plant, fatty acids of beeswax, fatty acids of lanolin or any of these which are hydrogenated. When R has any of these values, the compounds find particular usefulness in cosmetic compositions.

As is known, lanolin contains aliphatic acids having from 9 to 30 carbon atoms which are present in the form of n-alkanoic acids; isoalkanoic acids of the formula $(CH_3)_2—CH—(CH_2)_n—COOH$ wherein n can be 6, 8, 10, 12 or 14; anteisoalkanoic acids of the formula

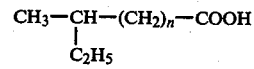

wherein n can be 4, 6, 8, 10, 12, 14, 16, 18, 20, 22, 24 or 26; 2-hydroxy-n-alkanoic acids; and 2-hydroxy-isoalkanoic acids.

The article by J. D. Van Dam et al, entitled, "New lanolin acid esters" in American Perfumer and Cosmetics, Vol. 84, August 1969, discloses a detailed composition of lanolin acids.

The present invention also relates to a two-stage process for preparing the compounds of formula (I). In the first stage, a diglycolamide of the formula R—CO—NH—CH$_2$—CH$_2$—O—CH$_2$—CH$_2$—OH (II) wherein R has the same meaning as in formula (I) above is prepared by condensing, at a temperature of 180°-210° C. and in particular from 190°-195° C., a diglycolamine (1) with a fatty acid of the formula R—COOH (III) wherein R has the meaning indicated above, or (2) with a lower alkyl ester, and preferably with a methyl or ethyl ester of the acid in formula (III) with elimination of the methyl or ethyl alcohol formed.

To obtain a diglycolamide of good quality, an excess of diglycolamine is employed, the residual diglycolamine then being removed, after condensation, by distillation under a vacuum. Advantageously 2 moles of diglycolamine per mole of fatty acid or per mol of ester are employed.

However, it is essential that the acid index of the diglycolamide thus prepared be as low as possible and preferably lower than 2, in order to avoid the formation of an alkaline soap during the condensation reaction of the said diglycolamide with glycidol.

In the second stage, n moles of glycidol are condensed on the diglycolamide obtained in the first stage. This condensation is carried out at a temperature between about 100° and 140° C., preferably between about 120° and 130° C., in the presence of an alkaline catalyst. There is preferably employed as the alkaline catalyst an alkaline hydroxide or alcoholate, for example, sodium or potassium hydroxide or alcoholate in an amount of 0.05 to 0.15 mole and preferably 0.08 mole, per mole of diglycolamide. Before introducing the glycidol into the reaction medium, alcohol or water originating from the catalyst, for example, when an alkaline alcoholate or hydroxide in the form of a concentrated alcoholic or aqueous solution is employed, is removed.

The glycidol is then progressively added in an inert atmosphere such as nitrogen to the molten diglycolamide, while regulating the temperature so as to compensate for the strong exothermicity of the reaction and to avoid any significant temperature increase. The reaction is practically instantaneous. The temperature of the reaction medium is maintained at about 120°–130° C. for about ½ hour after the end of the introduction of the glycidol. Generally, from 1 to 5 moles of glycidol are condensed per mole of diglycolamide. While it is possible to condense more than 5 moles of glycidol per mole of diglycolamide, this does not appear particularly desirable since water solubility of the diglycolamides is obtained generally for a value of n being from 1 to 5; n can be a whole or decimal number and it represents the average degree of polymerization. The process of the present invention provides a mixture of compounds all responding to general formula (I) and the number of molecules of glycidol fixed can be greater or less than the average degree of polymerization n.

The compounds thus prepared in accordance with the present invention are surface active agents which can be used as wetting agents, foaming agents, detergents, thickening agents, peptizers or emulsifying agents.

The compounds of the present invention having $C_8$–$C_{10}$ chains are wetting agents; those with $C_{12}$–$C_{14}$ chains and natural chains derived from copra and African oil palm acids are foams and detergents; those with $C_{16}$–$C_{20}$ chains or more complex ones such as those derived from lanolin acids are emulsifiers.

The polyhydroxyl amides of formula (I) exhibit, relative to oxyethylenated amides, the advantage of being more hydrophilic and their solubility is less dependent on the temperature. In effect, the solubility of oxyethylenated amide surface active agents diminishes as the temperature increases.

The invention also relates to a cosmetic composition in the form of an aqueous, hydroalcoholic or alcoholic solution. More specifically the cosmetic composition can be provided as a shampoo, a bath composition in the form of a foam, a suspension, a dispersion or an emulsion. The cosmetic composition thus comprises, a cosmetic vehicle suitable for application to the skin or the hair and one or more compounds of formula (I) in an amount of about 0.1 to 50% and generally from 0.1 to 30%, by weight of the total composition.

The composition of the present invention can also be provided in the form of a thickened solution or a gel.

These cosmetic compositions can include, in addition to the compounds of formula (I), conventional cosmetic adjuvants such as other non-ionic surface active agents or cationic, anionic, amphoteric or zwitterionic surface active agents, foam synergists, foam stabilizers, sequestering agents, super-fatting agents, thickening agents, emollients, antiseptics, preservatives, germicidal agents, dyes, perfumes and the like.

The cosmetic compositions of the present invention can have a pH ranging from 2.5 to 11, and preferably from 3 to 8.

The cosmetic compositions can also include a gaseous or liquified halohydrocarbon propellant, be packaged under pressure in an aerosol container and thus be provided as an aerosol formulation.

The following non-limiting examples illustrate the invention and unless otherwise stated all parts and percentages are by weight.

EXAMPLE 1

Preparation of compounds of formula (I) wherein R represents undecyl (derived from lauric acid) and n represents respectively, 2 and 1.5

First stage—Preparation of lauric diglycolamide

Into a 500 ml device, which can withstand heating to 200° C. and which can be adjusted for a distillation operation both at atmospheric pressure and under a vacuum, 200 parts (1 mole) of lauric acid and 210 parts (2 moles) of diglycolamine are introduced. The resulting mixture is heated under a nitogen atmosphere up to 190°–195° C. during which operation the water formed during the course of the reaction is distilled off. The reaction medium which is maintained at this temperature for 4 hours has an acid index equal to or less than 1.

Progressively then, a vacuum is established so as to distill the excess diglycolamine at 190° C. under 3 to 5 mm Hg.

The resulting diglycolamide has the following characteristics: Acid index, 0.4–1; Amine index, 1–3; and Hydroxyl index, 190–195.

Second stage—Condensation with glycidol

Into a 1000 ml device designed to distill under vacuum and fitted with a lead-in bulb, a thermometer and a nitrogen lead-in tube, 287 parts (1 mole) of lauric diglycolamide prepared in the first stage are introduced. There are then added 7.5 parts of a 49% aqueous solution of sodium hydroxide. A vacuum is established in the apparatus and the temperature of the reaction medium is elevated to 130° C. under 10–15 mm Hg, so as to completely remove the water. The vacuum is then broken by introducing a stream of nitrogen, and 148 parts (2 moles) of glycidol are progressively added to the reaction mixture through the bulb while cooling the reaction medium so as to maintain the temperature thereof at 130° C. The reaction is exothermic and essentially instantaneous.

The temperature of the reaction medium is maintained at 130° C. for ½ hour after the termination of the glycidol introduction.

The resulting product has the following characteristics: Hydroxyl index: 380–385 (Theory: 385); Acid index: 0; Kraft point at a concentration of 0.5% in water: 21°–22° C.; Cloud point at a concentration of 0.5% in water: >100° C.; and Cloud point at a concentration of 0.5% in a 10% aqueous NaCl solution: 46° C.

The second stage of the above process is repeated except that 1.5 moles, rather than 2 moles, of glycidol are condensed per mole of the diglycolamide.

The product obtained by this variation of the present process has a Kraft point of 24.5° C. in a 0.5% solution in water.

Following the procedures described above, other diglycolamides can be prepared, which other diglycolamides can be condensed in amounts ranging from 1 to 5 moles per mole of glycidol. The resulting compounds and their properties appear in the following table which has 8 columns. Column 1 identifies the diglycolamide prepared; columns 2, 3 and 4 list respectively the acid index, the amine index and the hydroxyl index of the thus prepared diglycolamide; columns 5 to 8 indicate the properties of the compounds of formula (I) thus prepared: column 5 gives the average degree of polymerization, n; column 6 lists the Kraft point in °C. at a concentration of 0.5% in water; column 7 recites the cloud point at a concentration of 0.5% in water; and column 8 recites the cloud point at a concentration of 0.5% in a 10% or 26% aqueous NaCl solution.

The compounds of formula (I) prepared from saturated fatty acids have a relatively high Kraft point.

It is possible to produce mixtures of the compounds of the present invention which forms a eutectic whose Kraft point is lower than 0° C. Representative mixtures include the following:

(1) a mixture of compounds of formula (I) where n has a statistical average value of 3 and which contains, per 100 parts by weight: 33.50 parts, where R is derived from lauric acid; 16.50 parts, where R is derived from myristic acid; 25 parts, where R is derived from oleic acid; and 25 parts, where R is derived from the fatty acids of copra; and (2) a mixture of compounds of formula (I) where n has a statistical average value of 3 and which contains per 100 parts by weight: 36.6 parts, where R is derived from lauric acid; 15.8 parts, where R is derived from myristic acid; and 47.6 parts, where R is derived from the fatty acids of copra.

foam and assists the untangling of wet hair. After drying, the hair is soft, shiny and agreeable to the touch. Other shampoo formulations of this type can be produced by varying the concentration of the compound of formula (I) between 3 and 20 weight percent and by varying the pH from 3 to 8.

EXAMPLE A-2—Shampoo composition

| | |
|---|---|
| Compound of formula (I) wherein R represents an undecyl radical derived from lauric acid and n is 2 | 5 g |
| Cellulose cationic polymer, sold under the mark "Polymer JR 400" | 1.7 g |
| $C_{18}H_{37}-N\begin{array}{l}(CH_2-CH_2-O)_x H \\ (CH_2-CH_2-O)_y H\end{array}$ wherein $x + y = 5$, sold under the mark "Ethomeen 18/15" | 0.3 g |
| Gelatin, sold under the mark "ASF/T" | 1 g |
| Lactic acid, q.s.p. pH = 7 | |
| Water, q.s.p. | 100 g |

A clear solution is thus produced which gives a soft

TABLE

| DIGLYCOLAMIDE Nature 1 | Acid Index 2 | Amine Index 3 | Hydroxyl Index 4 | COMPOUNDS OF FORMULA (I) | | |
|---|---|---|---|---|---|---|
| | | | | n 5 | Kraft Point (°C.) 6 | Cloud Point (°C.) Water 7 | Water + NaCl 8 |
| Lauric Acid | 0.4–1 | 1–3 | 190–195 | 1.5 | 24.5 | >100 | 25 x |
| | | | | 2 | 21–22 | >100 | 45–47 x |
| | | | | 3 | 19.5 | >100 | 52 x |
| Myristic Acid | 0.6 | 0.6 | 175 | 3 | 37–38 | >100 | 38 xx |
| Fatty Acids of Copra | 0.4–1 | 0.8–3 | 185–190 | 1.5 | 14 | >100 | 47 x |
| | | | | 3 | <0 | >100 | 68 xx |
| | | | | 4 | <0 | >100 | >100 xx |
| Hydrogenated Topped Fatty Acids of Copra (1) | (1)1.1 | 1.4 | 181 | 2.5 | 12 | >100 | 38 xx |
| Oleic Acid | 0.4 | 1.4 | 148–155 | 3 | <0 | >100 | 22 x |
| | | | | 4 | <0 | >100 | 15 xx and 63 x |
| Stearic Acid | 0.6 | 0.8 | 153 | 3 | 50 | >100 | — |
| Lanolin Acids (2) | 0 | 0 | 185 | 2 | <0 | >100 | 30 x | x Cloud point determined in a 10% aqueous NaCl solution
xx Cloud point determined in a 26% aqueous NaCl solution
(1) Topped fatty acids of copra is the product which results from removing the short $C_8-C_{10}$ chains from the fatty acids of copra Its composition is approximately as follows: $C_{12}$: 50%; $C_{14}$: 23%; $C_{16}$: 12%; $C_{18}$: 15%. Limited variations of these proportions are possible
(2) The diglycolamides of lanolin acids have been prepared by condensing on diglycolamine 1 mole of the fatty acids of lanolin (sold by Croda), having an acid index of 143 and a saponification index of 192. The diglycolamides thus prepared have been purified by removing the acid and basic products by passage over an ion exchange resin

EXAMPLES OF USE

EXAMPLE A-1—Shampoo Composition

| | |
|---|---|
| Compound of formula (I) wherein R represents a mixture of aliphatic radicals derived from topped fatty acids of copra oil and n is 2.5 | 15 g |
| Distearyl dimethylammonium chloride sold under the trade name "Cemulcat K 2 SH" | 0.4 g |
| Copra dimethyl ethoxy ammonium chloride | 1 g |
| Copra diethanolamide | 2 g |
| Glycol distearate | 2 g |
| Perfume | 0.1 g |
| Dye | 0.1 g |
| Lactic acid, q.s.p. pH = 3 | |
| Water, q.s.p. | 100 g |

This shampoo composition which has a pearly appearance, when applied to the head, provides abundant foam which is easily removed from the hair by rinsing. The thus treated hair combs easily and, after drying, possesses volume and liveliness, while remaining soft and easy to style.

EXAMPLE A-3—Liquid Bath Foam Composition

| | |
|---|---|
| Mixture of compounds of formula (I) wherein n has a statistical average value of 3 and which contains per 100 parts by weight: 33.5 parts of compounds where R is derived from lauric acid, 16.5 parts of compounds where R is derived from myristic acid, 25 parts of compounds where R is derived from oleic acid and 25 parts of compounds where R is derived from fatty acids of copra | 10 g |
| Sodium alkyl ether sulfate oxyethylenated with 2 moles of ethylene oxide | 10 g |

| | |
|---|---|
| Copra diethanolamide | 4 g |
| Compound of formula (I) wherein R represents a mixture of radicals derived from lanolin acids and n is 2 | 3 g |
| Dye | 0.1 g |
| Perfume | 0.1 g |
| Lactic acid, q.s.p. pH = 6.5 | |
| Water, q.s.p. | 100 g |

Other bath foam compositions of this type can be produced by varying the concentration of the compounds of formula (I) above, wherein n has a statistical average value of 3, from 5 to 20 weight percent and by varying the pH from 5 to 8.

EXAMPLE A-4—Beauty Cream

| | |
|---|---|
| Cetyl alcohol oxyethylenated with 6 moles of ethylene oxide, sold under the mark "BRIJ 56" | 5 g |
| Cetyl alcohol, pure | 5 g |
| Petrolatum oil, sold under the mark "MARCOL 82" | 20 g |
| Carboxyvinyl polymer, high mol. wt., sold under the mark "Carbopol 941" | 0.4 g |
| Glycerine | 5 g |
| Compound of formula (I) wherein R represents a mixture of radicals derived from lanolin acids and n is 2 | 1 g |
| Preservative | 0.3 g |
| Perfume | 0.3 g |
| Sterile demineralized water, q.s.p. | 100 g |

Method of preparation:

(1) The fatty phase which comprises a mixture of the oxyethylenated cetyl alcohol, the pure cetyl alcohol and the petrolatum oil is heated to 80° C.;

(2) A mixture of the major portion of water, the carboxy vinyl polymer and the glycerine which forms the aqueous phase is heated to 80° C.;

(3) The fatty phase and the aqueous phase are emulsified; and (4) The compound of formula (I) thinned in a small amount of water to avoid foaming is added thereto.

What is claimed is:

1. A compound of the formula:

R—CONH—CH$_2$—CH$_2$—O—CH$_2$—CH$_2$—O$\{$CH$_2$—CHOH—CH$_2$—O$\}_n$H wherein R represents an aliphatic radical or mixture thereof, linear or branched, saturated or unsaturated, optionally carrying one or more hydroxyl groups, having from 8 to 30 carbon atoms, of natural or synthetic origin; and n, representing a whole or decimal number from 1 to 5, represents the average degree of condensation.

2. The compound of claim 1 wherein R represents a mixture of radicals derived from fatty acids selected from the group consisting of (1) fatty acids of copra, (2) topped fatty acids of copra, (3) fatty acids of lanolin and (4) the hydrogenated acids of (1), (2) or (3).

3. A mixture of compounds of claim 1 having a Kraft point lower than 0° C.

4. The mixture of compounds of claim 3 which contains per 100 parts by weight: 33.50 parts where R is derived from lauric acid, 16.50 parts where R is derived from myristic acid, 25 parts where R is derived from oleic acid and 25 parts where R is derived from the fatty acids of copra and n has a statistical average value of 3.

5. A mixture of compounds of claim 3 which contains per 100 parts by weight: 36.6 parts where R is derived from lauric acid, 15.8 parts where R is derived from myristic acid and 47.6 parts where R is derived from the fatty acids of copra, and n has a statistical average value of 3.

6. A shampoo or bath foam composition comprising an aqueous solution of at least one compound of the formula:

R—CONH—CH$_2$—CH$_2$—O—CH$_2$—CH$_2$—O$\{$CH$_2$—CHOH—CH$_2$—O$\}_n$H wherein R represents an aliphatic radical or mixture thereof, linear or branched, saturated or unsaturated, optionally carrying one or more hydroxyl groups, having from 8 to 30 carbon atoms, of natural or synthetic origin, and n, representing a whole or decimal number from 1 to 5, represents the average degree of condensation, said compound being present in an amount of 0.1 to 50 weight percent based on the total composition.

7. The composition of claim 6 wherein R in said compound is a mixture of aliphatic radicals derived from topped fatty acids of copra oil and n is 2.5.

8. The composition of claim 6 wherein R is undecyl and n is 2.

9. The composition of claim 6 wherein said compound is present in an amount of 0.1 to 30 percent by weight of said composition.

10. The composition of claim 6 which also includes a cationic, anionic or another non-ionic surface active agent.

11. The composition of claim 6 which also contains at least one of a foam stabilizer, super-fatting agent, thickener, emollient or perfume.

12. A bath foam composition comprising an aqueous solution of a mixture of an effective amount of compounds of the formula R—CONH—CH$_2$—CH$_2$—O—CH$_2$—CH$_2$—O$\{$CH$_2$—CHOH—CH$_2$—O$\}_n$H where said mixture contains per 100 parts by weight, 33.5 parts where R is derived from lauric acid, 16.5 parts where R is derived from myristic acid, 25 parts wherein R is derived from oleic acid and 25 parts where R is derived from the fatty acids of copra, and n has a statistical average value of 3.

13. The bath foam composition of claim 12 which also includes an effective amount of another of said compounds wherein R is a mixture of aliphatic radicals derived from lanolin acids and n is 2.

14. In a beauty cream composition, in emulsion form, the improvement comprising, said beauty cream composition includes at least one compound of the formula R—CONH—CH$_2$—CH$_2$—O—CH$_2$—CH$_2$—O$\{$CH$_2$—CHOH—CH$_2$—O$\}_n$H wherein R represents an aliphatic radical or mixture thereof, linear or branched, saturated or unsaturated, optionally carrying one or more hydroxyl groups, having from 8 to 30 carbon atoms, of natural or synthetic origin, and n, representing a whole or decimal member from 1 to 5, represents the average degree of condensation, said compound being present in an amount of 0.1 to 50 weight percent based on the total composition.

15. The beauty cream composition of claim 14 wherein R in said compound is a mixture of aliphatic radicals derived from lanolin acids and n is 2.